United States Patent [19]

Midgley

[11] Patent Number: 5,304,296
[45] Date of Patent: Apr. 19, 1994

[54] GLASS PH ELECTRODES

[75] Inventor: Derek Midgley, Leatherhead, United Kingdom

[73] Assignee: National Power PLC, Swindon, United Kingdom

[21] Appl. No.: 961,935
[22] PCT Filed: Jun. 13, 1991
[86] PCT No.: PCT/GB91/00948
  § 371 Date: Feb. 11, 1993
  § 102(e) Date: Feb. 11, 1993
[87] PCT Pub. No.: WO92/01220
  PCT Pub. Date: Jan. 23, 1992

[30] Foreign Application Priority Data

Jul. 12, 1990 [GB] United Kingdom ............ 9015307

[51] Int. Cl.$^5$ ............................................. G01N 27/26
[52] U.S. Cl. ................................... 204/433; 204/416; 204/435; 204/153.21; 204/182.9
[58] Field of Search ........... 204/433, 435, 416, 153.21, 204/182.9

[56] References Cited

U.S. PATENT DOCUMENTS

| 4,175,020 | 11/1979 | Janata et al. | 204/435 |
| 4,279,724 | 7/1981 | Hearn et al. | 204/182.9 |
| 4,913,793 | 3/1990 | Leonard | 204/433 |

*Primary Examiner*—John Niebling
*Assistant Examiner*—Bruce F. Bell
*Attorney, Agent, or Firm*—Antonelli, Terry, Stout & Kraus

[57] ABSTRACT

A glass pH electrode which comprises a silver-silver chloride or a mercury-mercurous chloride inner electrode and an electrode filling solution for the inner electrode which is a zwitterionic buffer solution containing chloride ions.

5 Claims, No Drawings

GLASS PH ELECTRODES

The present invention relates to sensors which include an external reference electrode and a glass pH electrode, in particular a glass pH electrode with improved temperature characteristics.

Currently available sensors include glass electrodes which have characteristics that do not vary linearly with temperature, thus limiting the range over which the currently available pH meters can apply a temperature correction with a specified accuracy.

A pH meter is a voltmeter that measures the D.C. potential between a glass pH electrode and a reference electrode and converts the measurement so obtained into a pH value. The sensing and reference electrodes may be combined into a single unit or pH probe. The reference electrode supplies a known and stable reference potential against which the potential of the glass electrode may be measured. The difference between the glass electrode potential and the reference electrode potential varies in a manner which is known from the Nernst equation. The potential difference is a function of hydrogen ion activity and the "slope factor" which varies according to the Nernst equation.

The temperature compensation of pH measurements with glass electrodes is becoming of increasing importance as more measurements are made outside the laboratory, e.g. in environmental work, where temperatures in the range of from 0° to 10° C. are common, and in flue gas desulphurization liquors, where the temperature may be $\geq 50°$ C.

The ideal characteristics of a potentiometric pH cell (given that a non-zero temperature coefficient is inevitable) are listed below:

1. Slope factor (k) varies linearly with temperature, in accordance with the theoretical Nernst slope factor $$\partial k/\partial T = \frac{R}{F} \ln \qquad (10)$$

where R is the gas constant, T is the absolute temperature and F the Faraday constant.

2. The standard potential (E°) varies linearly with temperature.

3. The e.m.f. is independent of temperature at pH 7, i.e. the isopotential pH ($pH_{iso}$) has the value 7.0.

4. The pH at which the cell e.m.f. is zero should be 7.0.

5. The cell should have a low thermal capacity, enabling temperature equilibrium to be reached quickly.

6. The response to changes in temperature should be monotonic, i.e. if individual components of the cell have temperature coefficients of opposite sign, the design of the cell should not permit these components to change in temperature at such different rates that the overall cell e.m.f. changes direction en route to its new equilibrium value.

7. The system should not exhibit thermal hysteresis.

Apart from these characteristics, a pH cell must also satisfy the specification for measurement at constant temperature, e.g. precision, accuracy, range and freedom from interference.

Whilst characteristic (1) can be achieved and characteristic (4) presents relatively few problems in isolation, realizing characteristics (2) to (4) simultaneously is more difficult.

Characteristic (2) is rarely achieved in practice, because of the chemistry of the glass electrode's internal filling solution. In most cases this characteristic is assumed to be approximately achieved over a range of about 20° C.

Characteristics (5), (6) and (7) generally receive a low priority in the design of electrodes.

We have now developed a sensor including a glass pH electrode in which the linearity of the change in standard potential (characteristic (2)) is optimised, whilst generally satisfying the requirements of characteristics (3) and (4).

Accordingly, the present invention provides a sensor which includes an internal reference electrode and a glass pH electrode, the glass pH electrode comprising a silver-silver chloride or a mercury-mercurous chloride inner electrode and an electrode filling solution for the inner electrode, which electrode filling solution is a zwitterionic buffer solution containing chloride ions which is chosen so as to satisfy as nearly as possible one of the following a) when the inner electrode is a silver-silver chloride electrode and the external reference electrode is a non-isothermal calomel reference electrode the solution fulfills the requirements that $\partial pKa/\partial T = -0.0053 \pm 0.0034$: or b) when the inner electrode is a mercury-mercurous chloride electrode and the external reference electrode is a non-isothermal calomel reference electrode the solution fulfills the requirement that $\partial pKa/\partial T = -0.0088 \pm 0.0034$:

where pKa is the negative logarithm of the dissociation constant of the zwitterionic buffer, T is the absolute temperature and the filling solution for the external reference electrode is 3 mol $l^{-1}$ KCl.

The sensors of the present invention can, by suitable choice of the zwitterionic buffer and chloride concentration in the glass electrodes, be designed to have the desirable characteristics of zero-point and isopotential point both at a pH of approximately 7.0. (The isopotential pH is the pH at which the e.m.f. is the same at all temperatures).

Zwitterionic buffers which may be used in the present invention are detailed below.

| Buffer Acid | Abbr. | pKa at 20° C. | $\partial pKa/\partial T$ |
|---|---|---|---|
| 2-(N-morpholino)ethanesulphonic acid | MES | 6.15 | −0.011 |
| 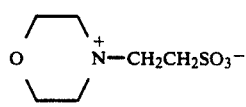 | | | |
| N-(2-acetamido)iminodiacetic acid | ADA | 6.62 | −0.011 |

-continued

| Buffer Acid | Abbr. | pKa at 20° C. | ∂pKa/∂T |
|---|---|---|---|

$$\overset{+}{H_3N}-\overset{O}{\overset{\|}{C}}-CH_2-\overset{+}{NH}\overset{CH_2COO^-}{\underset{CH_2COO^-}{<}}$$

| piperazine-N,N'-bis(2-ethanesulphonic acid | PIPES | 6.80 | −0.0085 |

$$^-O_3SCH_2CH_2-\overset{+}{NH}\underset{}{\overset{\frown}{\phantom{xx}}}\overset{+}{NH}-CH_2CH_2SO_3^-$$

The sensor may, if desired, comprise a combination electrode which has the glass electrode and the external reference electrode built into the same body, whilst being maintained electrochemically distinct as separate electrodes.

The present invention includes within its scope a pH meter which comprises a sensor as defined above.

The present invention will be further described with reference to the following non-limiting Examples.

GENERAL EXPERIMENTAL PROCEDURES

Apparatus

Potentials were measured with a digital pH meter reading to 0.1 mV and were simultaneously displayed on a chart recorder. Electrodes were fixed in sockets in the lids of water-jacketed glass cells connected to a Techne RB-5 thermocirculator.

Reference Electrode

A modified Kent 1352 calomel electrode with a remote ceramic frit junction was used. The main body of the electrode was fitted with a water-jacket connected to a Techne C-100 circulator at 25.0° C. The filling solution was 3 mol $l^{-1}$ KCl in each case.

Experimental Glass Electrode

Bodies from Kent 1070-1 standard glass electrodes were filled with various buffer solutions and fitted with appropriate reference electrodes.

Inner Silver-Silver Chloride Reference Electrodes

Irradiated polyolefin tubing (Radiospares 399-899) was heat-shrunk onto 1 mm diameter silver wire, leaving about 1 cm exposed at each end. The wire was then driven through a silicone rubber bung. One end was cleaned in ammonia, degreased with acetone and etched in hydrochloric acid; it was then anodized in 0.01 mol $l^{-1}$ nitric acid at 0.01 mA $cm^{-2}$ for 18 h.

Inner Mercury-Mercurous Chloride Reference Electrodes

Clear plastic tubing (Radiospares 399-899) was heat-shrunk onto 1 mm diameter platinum wire, leaving a 1 cm overlap at one end and 1 cm of exposed wire at the other. The wire was driven through a silicone rubber bung and then clamped vertically with the overlapping end of the PVC tubing uppermost and a small drop of mercury injected into the cavity from a syringe with a fine stainless steel needle. Electrolytic calomel (BDH) was added on top of the mercury and the tube plugged with cotton wool soaked in the appreciate filling solution. The mercury and calomel stayed in place when the electrode was turned the right way up and contact with the platinum wire was maintained.

Standard pH Solutions

Buffers were prepared from BDH Analar chemicals: 0.05 mol $kg^{-1}$ potassium hydrogen phthalate (pH 4.008 at 25° C.); 0.025 mol $kg^{-1}$ each of potassium dihydrogen phosphate and disodium hydrogen phosphate (pH 6.865 at 25° C.).

EXAMPLE 1

A solution of 0.05 mol $l^{-1}$ 2-(N-morpholino)ethanesulphonic acid, 0.025 mol $l^{-1}$ NaOH and 0.0453 mol $l^{-1}$ KCl (for Ag-AgCl reference electrodes) or 0.293 mol $l^{-1}$ KCl (for calomel reference electrodes) was prepared. The pH observed at 25° C. was 6.10 compared with 6.10 calculated. The solution was used as both the filling solution for the glass electrode and reference solution for the inner reference electrodes.

The temperature of the cell was then varied up and down and the steady values of the e.m.f.s. at each temperature were noted.

The target value of approximately 7.0 was achieved for the zero point pH for these combination.

The plot of E+kpH against k was linear for this electrode combination, with a slope of $pH_{iso}$ which is related to $\partial E°/\partial T$ by the following equation.

$$\partial E°_{cell}/\partial T = pH_{iso} \partial k/\partial T$$

The results are detailed below

| | Ag/AgCl Inner Reference Electrode | Hg/Hg$_2$Cl$_2$ Inner Reference Electrode |
|---|---|---|
| Slope factor (mV/pH) | −58.80 ± 0.28 | −58.77 ± 0.21 |
| Zero-point pH | 7.00 ± 0.05 | 7.1 |
| Isopotential pH | 5.8 ± 0.03 | 6.5 ± 0.2 |

EXAMPLE 2

A solution of 0.05 mol $l^{-1}$ N-(2-acetamido)iminodiacetic acid, 0.075 mol $l^{-1}$ NaOH and 0.140 mol $l^{-1}$ KCl was prepared. The pH observed at 25° C. was 6.59 compared with 6.57 calculated. The solution was used as both the filling solution for the glass electrode and the reference solution for both of the inner reference electrodes.

The temperature of the cell was then varied up and down and the steady values of the e.m.f.s. at each temperature were noted.

The plot of E+kpH against k was linear for this combination. The following results were obtained

|  | Ag/AgCl Inner Reference Electrode | Hg/Hg$_2$Cl$_2$ Inner Reference Electrode |
| --- | --- | --- |
| Slope factor | −58.85 ± 0.29 | −59.08 ± 0.17 |
| Zero-point pH | 7.2 | 8.0 |
| Isopotential pH | 5.9 ± 0.24 | 7.2 ± 0.46 |

EXAMPLE 3

A solution of 0.05 mol $1^{-1}$ piperazine-N,N'-bis(2-ethanesulphonic acid), 0.075 mol $1^{-1}$ NaOH and 0.226 mol $1^{-1}$ KCl (for Ag-AgCl reference electrodes) or 1.16 mol $1^{-1}$ KCl (for calomel reference electrodes) was prepared. The solution was used as both the filling solution for the glass electrode and the reference solution for both of the inner reference electrodes.

The temperature of the cell was then varied up and down and the steady values of the e.m.f.s. at each temperature were noted.

The plot of E+kpH against k was linear for this combination. The following results were obtained

|  | Ag/AgCl Inner Reference Electrode | Hg/Hg$_2$Cl$_2$ Inner Reference Electrode |
| --- | --- | --- |
| Slope factor | −58.89 ± 0.04 | −58.49 ± 0.07 |
| Zero-point pH | 7.2 ± 0.1 | 7.3 ± 0.03 |
| Isopotential pH | 5.0 ± 0.1 | 6.8 ± 0.28 |

I claim:

1. A sensor which includes an external reference electrode and a glass pH electrode, the glass pH electrode comprising a silver-silver chloride or a mercury-mercurous chloride inner electrode and an electrode filling solution for the inner electrode, characterized in that the electrode filling solution is a zwitterionic buffer solution containing chloride ions which is chosen so as to substantially satisfy one of the following a) when the inner electrode is a silver-silver chloride electrode and the external reference electrode is a non-isothermal calomel reference electrode the solution fulfills the requirement that $\partial pKa/\partial T = -0.0053 \pm 0.0034$; or b) when the inner electrode is a mercury-mercurous chloride electrode and the external reference electrode is a non-isothermal calomel reference electrode the solution fulfills the requirement that $\partial pKa/\partial T = -0.0088 \pm 0.0034$;

where pKa is the negative logarithm of the dissociation constant of the zwitterionic buffer, T is the absolute temperature and the filling solution for the external reference electrode is 3 mol $1^{-1}$ KCl.

2. A sensor as claimed in claim 1 wherein the glass pH electrode which has a zero-point and isopotential point both at a pH of approximately 7.0.

3. A sensor as claimed in claim 1 wherein the zwitterionic buffer satisfies case (a) and is 2-(N-morpholino)ethanesulphonic acid or N-(2-acetamido)iminoacetic acid.

4. A sensor as claimed in claim 1 wherein the zwitterionic buffer satisfies case (b) and is piperazine-N,N'-bis(2-ethanesulphonic acid).

5. A pH meter which comprises a sensor as claimed in any one of the preceding claims.

* * * * *